US011000389B2

(12) United States Patent
Bayer

(10) Patent No.: US 11,000,389 B2
(45) Date of Patent: May 11, 2021

(54) X-RAY MARKER AND ENDOPROSTHESIS WITH X-RAY MARKER

(71) Applicant: BIOTRONIK AG, Buelach (CH)

(72) Inventor: Ullrich Bayer, Bad Doberan (DE)

(73) Assignee: BIOTRONIK AG, Buelach (CH)

( * ) Notice: Subject to any disclaimer, the term of this patent is extended or adjusted under 35 U.S.C. 154(b) by 429 days.

(21) Appl. No.: 15/262,957

(22) Filed: Sep. 12, 2016

(65) Prior Publication Data

US 2017/0119555 A1 May 4, 2017

(30) Foreign Application Priority Data

Nov. 4, 2015 (DE) .......................... 10 2015 118 859

(51) Int. Cl.
*A61F 2/82* (2013.01)

(52) U.S. Cl.
CPC ........ *A61F 2/82* (2013.01); *A61F 2250/0098* (2013.01); *A61F 2310/00131* (2013.01); *A61F 2310/00137* (2013.01)

(58) Field of Classification Search
CPC .............................................. A61F 2250/0098
See application file for complete search history.

(56) References Cited

U.S. PATENT DOCUMENTS

| | | | |
|---|---|---|---|
| 6,293,966 B1 | 9/2001 | Frantzen | |
| 6,355,058 B1* | 3/2002 | Pacetti | A61L 29/18 427/2.25 |
| 2004/0267203 A1 | 12/2004 | Potter et al. | |
| 2007/0043429 A1* | 2/2007 | Hegel | A61F 2/82 623/1.15 |
| 2011/0319982 A1* | 12/2011 | Bayer | A61L 31/022 623/1.34 |
| 2015/0148891 A1 | 5/2015 | Dugan et al. | |
| 2016/0228267 A1* | 8/2016 | Pacetti | A61F 2/82 |

FOREIGN PATENT DOCUMENTS

| | | |
|---|---|---|
| DE | 69836656 T2 | 9/2007 |
| EP | 1570808 B1 | 9/2005 |
| EP | 2184038 A2 | 5/2010 |

OTHER PUBLICATIONS

Pitsch-Machacek, Christa, "Search Report dated Mar. 22, 2016", German Patent Office, Mar. 22, 2016, 7 pages.

* cited by examiner

*Primary Examiner* — Jacqueline Woznicki
(74) *Attorney, Agent, or Firm* — Greer, Burns & Crain, Ltd.; Steven P. Fallon

(57) ABSTRACT

An x-ray marker for an endoprosthesis and an endoprosthesis with an x-ray marker are provided. The endoprosthesis includes a hollow cylinder made of a first radiopaque metal and a marker element, which is fixedly connected to the hollow cylinder and which is arranged inside the hollow cylinder and consists of a second radiopaque metal. The marker element can be a metal powder or in the form of metal particles which is/are embedded in the electrically non-conductive material. The marker element can be solid cylinder with a diameter smaller than the inner diameter of the hollow cylinder and the electrically non-conductive material can form a layer between an inner lateral surface of the hollow cylinder and a lateral surface of the solid cylinder.

16 Claims, 2 Drawing Sheets

X-RAY MARKER AND ENDOPROSTHESIS WITH X-RAY MARKER

PRIORITY CLAIM

This application claims priority under 35 U.S.C. § 119 and all applicable statutes and treaties from prior German Application DE 10 2015118 859.7, filed Nov. 4, 2015.

FIELD OF THE INVENTION

A field of the invention is endoprosthesis devices with x-ray markers, including endovascular stents, and particularly biodegradable stents.

BACKGROUND

Stents are endovascular prostheses which can be used for the treatment of stenoses (vasoconstrictions). They have a main body in the form of a hollow-cylindrical or tubular basic mesh, which is open at both longitudinal ends of the tube. The tubular basic mesh of an endoprosthesis of this type is inserted into the vessel to be treated and serves to support the vessel.

Stents of this type or other endoprostheses often have a main body made of a metallic material. For the present invention, biodegradable metallic materials are of particular significance. Here, biodegradation means hydrolytic, enzymatic or metabolic degradation processes in the living organism which are caused primarily by the bodily fluids coming into contact with the endoprosthesis and lead to a gradual dissolution of at least large parts of the endoprosthesis. The term biocorrosion is often used synonymously with the term biodegradation. The term bioabsorption includes the subsequent absorption of the degradation products by the living organism. Materials suitable for the main body of biodegradable endoprostheses include, for example, alloys of magnesium, iron, zinc and tungsten.

X-ray diagnostics constitutes an important instrument for post-operative monitoring of the healing progress or for monitoring minimally invasive interventions. By way of example, for some years now, stents have been placed in the coronary arteries in the case of acute myocardial infarction therapy. A catheter which supports the stent in a non-expanded state is positioned in the region of the lesion of the coronary vessel wall in accordance with conventional methods. The stent then expands either by means of self-expanding forces or by inflation of a balloon, in order to prevent an obstruction of the vessel wall in the expanded state. The process of the positioning and expansion of the stent must be monitored continuously by the cardiologist during the procedure.

X-ray beams in the energy range from 60 to 120 keV are used in the medical field, and those in the range from 80 to 100 keV are used in the event of application to the heart. Since the x-ray absorption coefficient is heavily dependent on the energy, this working range must be taken into consideration when choosing suitable marker materials. The absorption (attenuation of intensity) of the x-ray beams can be described in simple terms by means of an exponential attenuation law.

$$\frac{I}{I_O} = \exp\left[-\left(\frac{\mu}{\rho}\right)x\right]$$

Here, I is the measured intensity once the radiation has passed through the sample, $I_O$ is the intensity of the radiation before passing through the sample, $\mu/\rho$ is the mass absorption coefficient, and x is the material thickness of the sample. For alloys, the mass absorption coefficient is calculated by summation of the components.

With low absorption of the selected material in a given energy range of x-ray absorption, an improvement of the x-ray visibility could therefore be achieved by increasing the material thickness; this measure, however, quickly reaches its limits, in particular when it comes to the marking of filigree structures as are present in the case of stents.

It is therefore known to provide implants with a marker in the form of a coating, a band, an inlay or another integrally formed design for improving the x-ray visibility. By way of example, metal bands made of gold or other noble metals are applied to certain regions of a stent. Examples of x-ray markers of this type can be inferred from EP 2 184 038 A2, US 2007/0043429 A1 and EP 1 570 808 B1.

In the case of implants made of biocorrodible metallic materials—for example based on magnesium, iron, zinc or tungsten—further requirements are placed on the marker material:

the marker should not be separated prematurely from the main body of the implant by the corrosive processes, so as to prevent fragment formation and therefore a risk of embolization;

the marker should have a sufficient radiopacity even with low material thicknesses; and the marker material should have as little influence as possible or at most only a small influence on the degradation of the main body.

In the case of stents of which the main body consists of a metallic material, a problem encountered with the arrangement of x-ray markers, for example radiopaque elements made of gold, on the main body of the stent is that contact corrosion occurs at the region of contact between the material of the main body and the material of the functional element. This leads to the destruction of the stent or to the separation of the x-ray marker from the stent structure, such that the endoprosthesis is no longer able to perform its function or can no longer be found. In the case of main bodies made of magnesium, x-ray markers made of gold or platinum cannot be used on account of their very pronounced local element effect. The problem of local element formation is also encountered in the case of x-ray markers made of different metallic components.

Document U.S. Pat. No. 6,355,058 B1 describes a stent in which radiopaque markers are enclosed as particles in a polymeric binder. The binder is spread (dispersed) over the surface of the stent. A distribution of this type of radiopaque particles generally does not provide a sufficient density of these materials, and therefore the x-ray visibility is too low for many applications.

In document U.S. Pat. No. 6,293,966 B1 a stent having radiopaque marker elements is disclosed, which at its distal and proximal ends has C-shaped elements, which each form a substantially spherical receptacle. Marker elements having spherical end portions are inserted into these receptacles. The spherical end portions are secured in the receptacles formed by the C-shaped elements in an interlocking manner and by means of a welded connection where appropriate.

Document DE 698 36 656 T2 describes a bioabsorbable marker having radiopaque constituents for use on an implantable endoprosthesis, such as a stent. The bioabsorbable radiopaque markers for example have porous portions, which are filled with radiopaque material. In addition, a marker is described which has hollow, cavity-like and porous portions, which are filled with radiopaque material. In addition, a marker is presented in the prior art which is formed as an elongate element such as a filament and which is looped around parts of the implantable endoprosthesis.

The introduction (riveting, laser welding or electron beam welding) of markers in the form of round blanks or pellets (diameter <400 µm) is also very demanding from a technical point of view and requires complex handling technology. With contact of local material compounds, as are present in the case of a welded connection, what is known as a stress shielding effect is produced as a result; this means that the greater the difference between the moduli of elasticity of the connected metal materials, the greater are the mechanical stresses at the interfaces under bending load and/or torsional load. These are based on the different deformation behavior of the materials under mechanical load. This can result in failure of the material compound and can therefore lead to the loss of the marker.

SUMMARY OF THE INVENTION

An x-ray marker includes a hollow cylinder made of a first radiopaque metal and a marker element. The marker element is fixedly connected to the hollow cylinder and is arranged inside the hollow cylinder. The marker element consists of a second radiopaque metal or an alloy thereof. An electrically non-conductive material is located between the marker element and the hollow cylinder. In preferred embodiments, the marker element is present as metal powder or in the form of metal particles which is/are embedded in the electrically non-conductive material. In preferred embodiments, the marker element is a solid cylinder with a diameter smaller than the inner diameter of the hollow cylinder and the electrically non-conductive material forms a layer between an inner lateral surface of the hollow cylinder and a lateral surface of the solid cylinder.

BRIEF DESCRIPTION OF THE DRAWINGS

The invention will be explained in greater detail hereinafter on the basis of exemplary embodiments illustrated in the drawings, in which.

DETAILED DESCRIPTION OF THE PREFERRED EMBODIMENTS

Figure 1:
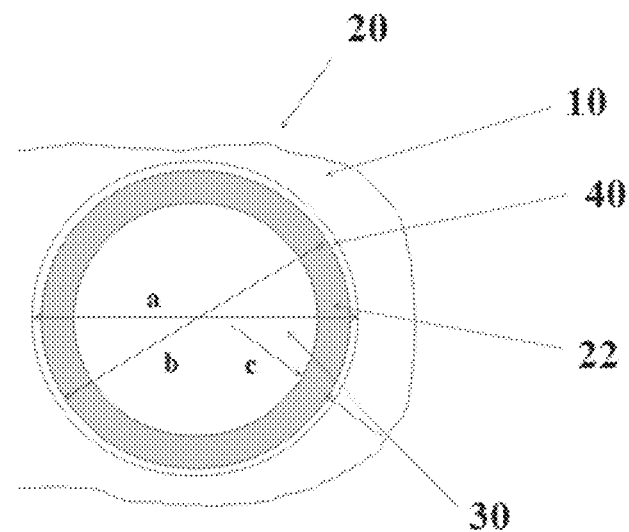
FIG. 1 shows a schematic plan view of an endoprosthesis with an x-ray marker in accordance with a first embodiment according to the invention.

One or more disadvantages of the prior art are solved or at least mitigated with the aid of the x-ray marker according to the invention. The x-ray marker includes a hollow cylinder made of a first radiopaque metal and a marker element, which is fixedly connected to the hollow cylinder and which is arranged inside the hollow cylinder. In a preferred embodiment the marker element consists of a second radiopaque metal or an alloy thereof. The metals used for the hollow cylinder and the further marker element are therefore different. Due to the use of different metals, local elements can be heavily reduced already through material selection. If, for example, the hollow cylinder material is selected to be chemically similar to the endoprosthesis material, local element effects in the case of metallic contact with the body of the endoprosthesis can be minimized. However, the endoprosthesis is also characterized in that an electrically non-conductive material is located between the marker element and the hollow cylinder. Undesirable electrochemical processes between the metals of the hollow cylinder and of the marker element can thus be effectively prevented.

The x-ray markers according to the invention can thus be pre-fabricated with different dimensions, placed in a store, and introduced into different endoprostheses as required, and also can be adapted to different patient sizes, since more or less x-ray radiation is absorbed merely on account of different body masses and associated penetration depths. During storage, corrosive processes between the different metallic components of the marker are eliminated by the separation by means of the non-conductive material, even in the presence of moisture. A corrosive behavior of this type is effectively prevented in vivo as well. Furthermore, the x-ray marker proposed herein offers the possibility of adapting the x-ray visibility not only to patients, but also to the future machine standard of the x-ray machines, and therefore of providing x-ray markers also tailored for the future, both by material selection and by effective material density. Is also advantageous that otherwise necessary and costly plating processes, which often have to be carried out even in the case of non-absorbable metals, are omitted.

A hollow cylinder in the meaning of the present invention is not restricted to the classical form of a straight tube having a circular surface. A hollow cylinder can adopt any form including circular, elliptic, ellipsoid, triangular, quadratic, rectangular, polyangular, eight-shaped or also completely irregular shapes as long as at least one plane is enclosed by the surrounding walls. Two opposing surfaces defining the hollow volume can also have different shapes. A connection between the surfaces defining the hollow volume need not be joined rectangularly to the surfaces and the opposing surfaces need not be parallel to each other. A hollow cylinder can describe a protruding volume which is preferably tubular.

A marker element can adopt any conceivable shape as long as the marker element can be inserted into the volume of the hollow cylinder. In that, completely irregular shapes such as powder particles can be adopted as well as solid cylinders which custom-fit into the hollow cylinder as well as spherical particles.

In accordance with a preferred variant the marker element is present as metal powder or in the form of metal particles. The metal powder or the metal particles is/are embedded here into the electrically non-conductive material. In order to produce the x-ray marker, simply a composite of metal powder or particles and electrically non-conductive material can therefore be introduced into the interior of the hollow cylinder. A proportion by weight of the metal in the composite should preferably lie in the range from 45 to 97%, preferably 60 to 93%. Here, the marker element is embedded in the composite such that there is no metal-metal contact between the marker element and hollow cylinder. This can be achieved well when the proportion by weight of the metal in the composite does not exceed 97% and the composite has been thoroughly mixed prior to insertion into the cylinder. Due to the thorough mixing, it is ensured that the metal powder grains or metal particles are encompassed by the electrically non-conductive material. Due to the good mixing and the electrical insulation of the metal powder grains or metal particles, the marker element can be filled into the hollow cylinder favorably in terms of the method employed, even without further steps, if allowed by the consistency of the composite. Electrical insulation between the hollow cylinder and marker element can also be achieved preferably by applying the non-conductive material either to the outer side of the marker element or to the inner side of the hollow cylinder prior to the insertion of the marker element.

In accordance with a further preferred variant the marker element is a solid cylinder with a diameter smaller than the inner diameter of the hollow cylinder. The electrically non-conductive material here forms a layer between an inner lateral surface of the hollow cylinder and a lateral surface of the solid cylinder. The solid cylinder ensures a sufficiently high x-ray visibility. The peripheral layer in particular has a layer thickness in the range from 7.5-15 μm. Effective electrical insulation and good adhesion of the solid cylinder to the hollow cylinder are preferably achieved in this layer thickness range without unnecessarily increasing the dimensions of the x-ray marker.

In order to improve the adhesion the inner lateral surface of the hollow cylinder and the lateral surface of the solid cylinder preferably have a roughness value Ra in the range of 0.4-2 μm, more preferably from 0.6 to 1.2 μm. Good adhesion can contribute to the fact that, even with a low wall thickness, the forces that would detach the x-ray marker from the bond with the endoprosthesis under mechanical load are high and therefore a high bond strength is generated. The likelihood of the undesirable loss of the marker is thus considerably reduced It is also preferred when the hollow cylinder consists of tungsten, tantalum or alloys of these metals. Furthermore, the hollow cylinder can have a diameter in the range of 100-500 μm and a height in the range of 50-180 μm. It is additionally preferred when the hollow cylinder has a wall thickness in the range of 10-50 μm. With these dimensions and materials, a sufficiently good x-ray visibility can be achieved without having to accept an unnecessary material expenditure.

The electrically non-conductive material is preferably a polymer adhesive. Suitable polymer adhesives preferably include polyurethanes, silicons, polymethyl methacrylates, cyanoacrylates, polyesters and epoxy resins.

In a preferred embodiment elastic polymer adhesives are used. Suitable elastic adhesives include silicons, polylactides, polyhdroxybutyrate and blends thereof. Elastic adhesives have the advantage that they contribute to an improved trackability, that is to say to an adaptation to the surrounding tissue during the advance of the endoprosthesis as this is inserted. A premature loss of an x-ray marker is thus made even more unlikely.

The marker element, in particular in the embodiment of a solid cylinder, can consist in particular of gold, platinum, iridium or alloys thereof, that is to say metals which have particularly good radiopaque properties, but are also costly. If the hollow cylinder is formed from tantalum or alloys thereof, the marker element preferably consists of tungsten. Due to the compact design with simultaneous insulation for the prevention of local elements, an x-ray marker can be constructed here economically.

In a preferred embodiment a particularly wide energy range of x-ray beams can be absorbed advantageously by suitable selection of the materials for the hollow cylinder and marker element. In a preferred embodiment the hollow cylinder is manufactured from tantalum or alloys thereof and the marker element is produced from gold or platinum. In a further preferred embodiment the hollow cylinder is manufactured from tungsten and the marker element is manufactured from gold. It is particularly preferred when the hollow cylinder is manufactured from tantalum and the marker element is manufactured from gold.

A further aspect of the invention lies in providing an endoprosthesis having a metallic main body and having at least one x-ray marker according to the invention secured to the main body. The main body preferably consists of a biodegradable, metallic material, in particular a magnesium alloy. An electrically non-conductive material, in particular a polymer adhesive, is preferably located between the x-ray marker and the main body and prevents corrosive processes between the two metal materials. An assembly process can be simplified by gluing pre-fabricated markers into defined receptacles on the endoprosthesis.

In a preferred embodiment the electrically non-conductive material can be provided in the form of a layer between the hollow cylinder and endoprosthesis. In a further preferred embodiment the layer made of electrically non-conductive material has a thickness of more than 5 μm and preferably a thickness of 7.5-15 μm.

It has been found advantageously that, by introducing two insulating layers, wherein one is arranged between the marker element and hollow cylinder and the second is arranged between the hollow cylinder and the endoprosthesis, a complete or approximately complete elimination of the creation of galvanic elements and therefore associated current flows caused by local element formation can be achieved. An endoprosthesis of this type thus has a significantly improved service life and compatibility, as well as a reduced risk of prematurely losing an x-ray marker in an uncontrolled manner. These markers can also be used in endoprostheses made of a wide range of materials with no risk of negative interactions between the used materials.

In a further embodiment an endoprosthesis having a metallic main body and having at least one x-ray marker according to the invention secured to the main body is proposed, wherein the metallic main body has a multiple marker, in particular a double marker, at least at the proximal and distal end. A multiple marker, in particular a double marker, in this case comprises at least two adjacent different x-ray markers according to the invention, and in the case of a double marker two different x-ray markers according to the invention. The different x-ray markers according to the invention differ from one another here by the choice of the materials for the hollow cylinder and the marker element, but in particular by the choice for the material of the marker element. An endoprosthesis is thus proposed having a metallic main body and having at least one x-ray marker according to the invention secured to the main body, wherein the metallic main body has a multiple marker at least at the proximal and distal end, wherein the multiple marker comprises at least two adjacent different x-ray markers according to the invention, and preferably wherein the at least two adjacent different x-ray markers according to the invention have different marker elements.

In an exemplary embodiment an endoprosthesis of the type proposed here comprises a double marker both at the distal and proximal end, wherein the hollow cylinders of a double marker are fabricated from tantalum, whereas the marker elements are fabricated from tungsten or from platinum or in an alternative embodiment from gold and platinum.

An embodiment of this type of an endoprosthesis comprising multiple markers as described herein has the advantage that it is ensured that, with different x-ray machines, an optimal x-ray visibility can be generated. By way of example, the specifications (with a certain acceleration voltage range xxx) of the x-ray machine yyy lead to an improved visibility of the tungsten marker. Another x-ray machine zzz (having a different acceleration voltage range aaa) better shows the markers made of gold and/or platinum. Device independence is thus produced for the x-ray visibility.

In accordance with the present proposal, an endoprosthesis can thus be provided which has protection (proposed herein) against local elements and in addition is characterized by optimal x-ray visibility.

FIG. 1 shows a considerably enlarged portion of a main body 10 of an endoprosthesis, in particular of a stent. The main body 10 (not illustrated here in greater detail) has, as support elements, webs folded in a zigzag or meandering form and extending substantially in the peripheral direction or helical webs and also has, as connecting elements, webs extending substantially in the longitudinal direction of the stent. The portion illustrated in FIG. 1 is part of a structural element serving to receive an x-ray marker 20. The main body 10 consists for example of a biodegradable magnesium alloy. The round receptacle on the frame has a diameter a, for example of approximately 350 μm, and has a web wall thickness, for example of approximately 120 μm. The x-ray marker 20 illustrated in FIG. 1 has a hollow cylinder 22 made of tantalum, the interior of which is filled with a composite 30 formed from a marker element and an electrically non-conductive material. Here, the marker element is embedded in the composite such that there is no metal-metal contact between the marker element and hollow cylinder. The x-ray marker 20 is connected to the main frame 10 by an insulating adhesive layer 40.

The x-ray marker 20 can be produced as follows:

A tube portion formed from 99% pure tantalum is cut to a suitable length, for example 150 μm. An outer diameter b of the tube portion b can be 310 μm, for example, and the wall thickness c of the tube can also be 50 μm, for example. The resultant inner diameter in the example described here is thus 210 μm. The inner and outer surfaces are sandblasted, then thermally oxidized, and have a suitable roughness value of Ra=0.8 μm, for example.

A metal powder/polymer compound is then produced, having the following ingredients in a ratio of 92% by weight metal powder and 8% by weight polymer:
metal powder: Au, mean particle size 15 nm
polymer: silicone adhesive MED2-4213 (manufactured by NUSIL Technology)

Once the individual components have been weighed, the components are manually stirred and then blended in centrifuges in order to produce a homogenous mixture. The mixture is filled into cartridges and injected into the tantalum tube via a cannula without air inclusions. The mixture is then cured in a temperature-control chamber at 150° C. for 15 min.

A number of these tube portions, which are now filled, with the cured inlay are introduced upright into a template and ground down to a nominal height of 120 μm on grinding discs.

Figure 2:
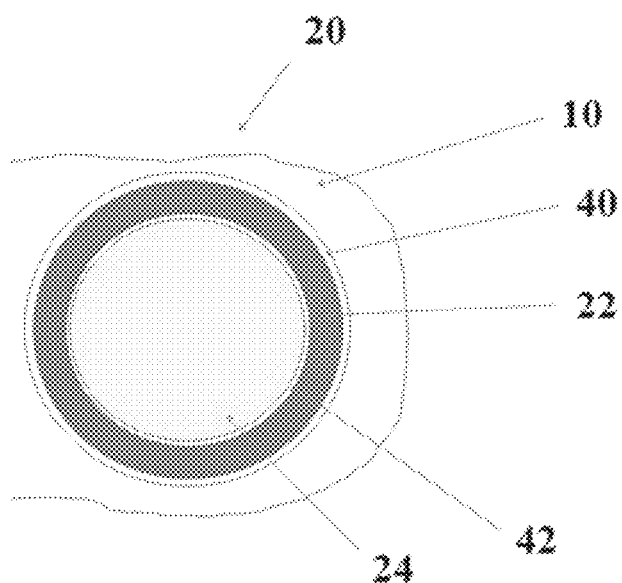
FIG. 2 shows a schematic plan view of an endoprosthesis with an x-ray marker in accordance with a second embodiment according to the invention.
Figure 3:
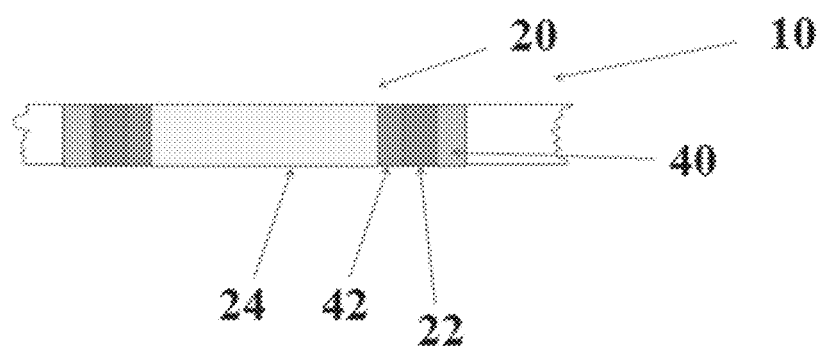
FIG. 3 shows a sectional view through the x-ray marker illustrated in FIG. 2.

FIGS. 2 and 3 show a further embodiment of the x-ray marker 20. The main frame 10 and adhesive layer 40 can be embodied similarly to the embodiment illustrated in FIG. 1, wherein alternative dimensions can be applied here as well. For example, deviating from the exemplary embodiment of FIG. 1, the diameter of the receptacle can thus be 450 μm and the main frame 10 can have a web wall thickness of 100 μm. The hollow cylinder 22 consists here of tungsten; however, it can also be produced from other suitable materials. A solid cylinder 24 forms a further marker element inside the hollow cylinder 22. The solid cylinder 24 has a diameter smaller than the inner diameter of the hollow cylinder 22. The resultant gap is filled with an electrically non-conductive material, which forms a layer 42.

The x-ray marker 20 can be produced as follows:

A tube portion formed from 99% tungsten is cut to a length of 130 μm. An outer diameter of the tube portion is 410 μm, and the wall thickness is 80 μm. The resultant inner diameter is 250 μm. The inner and outer surfaces are sandblasted, then thermally oxidized, and have a suitable roughness value of Ra=0.8 μm, for example.

A round blank (solid cylinder) made of pure gold (99%) with an outer diameter of 220 μm and a height of 130 μm is also provided. The round blank is dipped in a polymer solution of the silicone adhesive MED2-4213 (manufactured by NUSIL Technology) and is then brought into the tungsten tube portion. Curing is performed in a temperature-control chamber at 150° C. for 15 min. A number of these filled tube portions are brought upright into a template and ground down on both sides to a nominal height of 120 μm on grinding discs.

In accordance with a further variant for the previously described embodiment, the main frame can consist of nitinol, the x-ray marker with a hollow cylinder can consist of tantalum, and a round blank can consist of platinum. Alternatively, the main frame can consist of CoCr (L605), the x-ray marker with a hollow cylinder can consist of tungsten, and a round blank can consist of gold.

The invention claimed is:

1. An x-ray marker for an endoprosthesis, consisting of:
   a hollow cylinder consisting of a first radiopaque metal, the first radiopaque metal consisting of tungsten, tantalum or alloys thereof;
   a marker element fixedly connected to the hollow cylinder and arranged inside the hollow cylinder, the marker element consisting of a second radiopaque metal or an alloy thereof, and
   an electrically non-conductive material located between the marker element and the hollow cylinder.

2. The x-ray marker as claimed in claim 1, wherein the second radiopaque metal or an alloy thereof is a metal powder or metal particles, and the metal powder or metal particles are embedded in the electrically non-conductive material.

3. The x-ray marker as claimed in claim 1, wherein the second radiopaque metal or an alloy thereof is a solid cylinder with a diameter smaller than the inner diameter of the hollow cylinder, and the electrically non-conductive material forms a peripheral layer between an inner lateral surface of the hollow cylinder and a lateral surface of the solid cylinder.

4. The x-ray marker as claimed in claim 3, wherein the peripheral layer has a layer thickness in the range of 7.5-15 μm.

5. The x-ray marker as claimed in claim 3, wherein the inner lateral surface of the hollow cylinder and the lateral surface of the solid cylinder have a roughness Ra in the range of 0.4-2 μm.

6. The x-ray marker as claimed in claim 1, wherein the hollow cylinder has a diameter in the range of 100-500 μm and a height in the range of 50-180 μm.

7. The x-ray marker as claimed in claim 1, wherein the hollow cylinder has a wall thickness in the range of 10-50 μm.

8. The x-ray marker as claimed in claim 1, wherein the electrically non-conductive material is a polymer adhesive.

9. The x-ray marker as claimed in claim 1, wherein the second radiopaque metal or an alloy thereof consists of gold, platinum, iridium or alloys thereof.

10. The x-ray marker as claimed in claim 1, wherein the second radiopaque metal or an alloy thereof consists of tungsten and the hollow cylinder is formed from tantalum or alloys thereof.

11. An endoprosthesis having a metallic main body and having at least one x-ray marker as claimed in claim 1 secured to the main body.

12. The endoprosthesis as claimed in claim 11, wherein the main body consists of a biodegradable, metallic material.

13. The endoprosthesis as claimed in claim 11, wherein an insulating adhesive material is located between the x-ray marker and the main body.

14. The endoprosthesis as claimed in claim 11, wherein the at least one x-ray marker comprises multiple x-ray markers arranged on the metallic main body at least at a proximal and a distal end thereof, wherein the multiple x-ray markers comprise at least two adjacent different x-ray markers.

15. An x-ray marker for an endoprosthesis, comprising:
- a hollow cylinder consisting of a first radiopaque metal, the first radiopaque metal consisting of tungsten, tantalum or alloys thereof;
- a marker element fixedly connected to the hollow cylinder and arranged inside the hollow cylinder, the marker element consisting of a second radiopaque metal or an alloy thereof, and
- an electrically non-conductive material located between the marker element and the hollow cylinder.

16. The x-ray marker as claimed in claim 1, wherein the hollow cylinder is filled by the marker element and the electrically non-conductive material.

\* \* \* \* \*